(12) United States Patent
Maeda

(10) Patent No.: US 8,961,761 B2
(45) Date of Patent: Feb. 24, 2015

(54) OXYGEN SENSOR CONTROL APPARATUS

(71) Applicant: NGK Spark Plug Co., Ltd., Nagoya-shi, Aichi-ken (JP)

(72) Inventor: Seiji Maeda, Inazawa (JP)

(73) Assignee: NGK Spark Plug Co., Ltd., Aichi (JP)

( * ) Notice: Subject to any disclaimer, the term of this patent is extended or adjusted under 35 U.S.C. 154(b) by 99 days.

(21) Appl. No.: 13/796,723

(22) Filed: Mar. 12, 2013

(65) Prior Publication Data

US 2013/0255232 A1   Oct. 3, 2013

(30) Foreign Application Priority Data

Mar. 13, 2012  (JP) ................. 2012-056213

(51) Int. Cl.

| | |
|---|---|
| F02D 41/02 | (2006.01) |
| F01N 11/00 | (2006.01) |
| G01N 27/406 | (2006.01) |
| F02D 41/14 | (2006.01) |

(52) U.S. Cl.
CPC .......... *F01N 11/007* (2013.01); *G01N 27/4065* (2013.01); *F02D 41/1455* (2013.01); *F02D 41/1494* (2013.01); *Y02T 10/47* (2013.01); *F01N 2560/025* (2013.01); *F02D 41/1454* (2013.01)
USPC .......................................... 204/424; 204/406

(58) Field of Classification Search
None
See application file for complete search history.

(56) References Cited

U.S. PATENT DOCUMENTS 5,852,228 A   12/1998   Yamashita et al.
5,974,857 A   11/1999   Yamashita et al.

FOREIGN PATENT DOCUMENTS

JP             10-26599 A         1/1998

*Primary Examiner* — J. Christopher Ball
(74) *Attorney, Agent, or Firm* — Sughrue Mion, PLLC

(57) ABSTRACT

An oxygen sensor control apparatus includes internal resistance detection means S3, controlled internal resistance obtaining means S4 to S11, and heater energization control means S12. When a timing for detecting the internal resistance R(n) comes during a lean period TL, the controlled internal resistance obtaining means uses the detected internal resistance R(n) as the controlled internal resistance Rf. When a timing for detecting the internal resistance R(n) comes during a rich period TR, the controlled internal resistance obtaining means uses, as the controlled internal resistance Rf, a value obtained by correcting the detected internal resistance R(n) on the basis of a latest lean resistance R(k) such that a variation of the internal resistance which stems from the difference between the lean state and the rich state and which is contained in the detected internal resistance R(n) is removed.

3 Claims, 6 Drawing Sheets

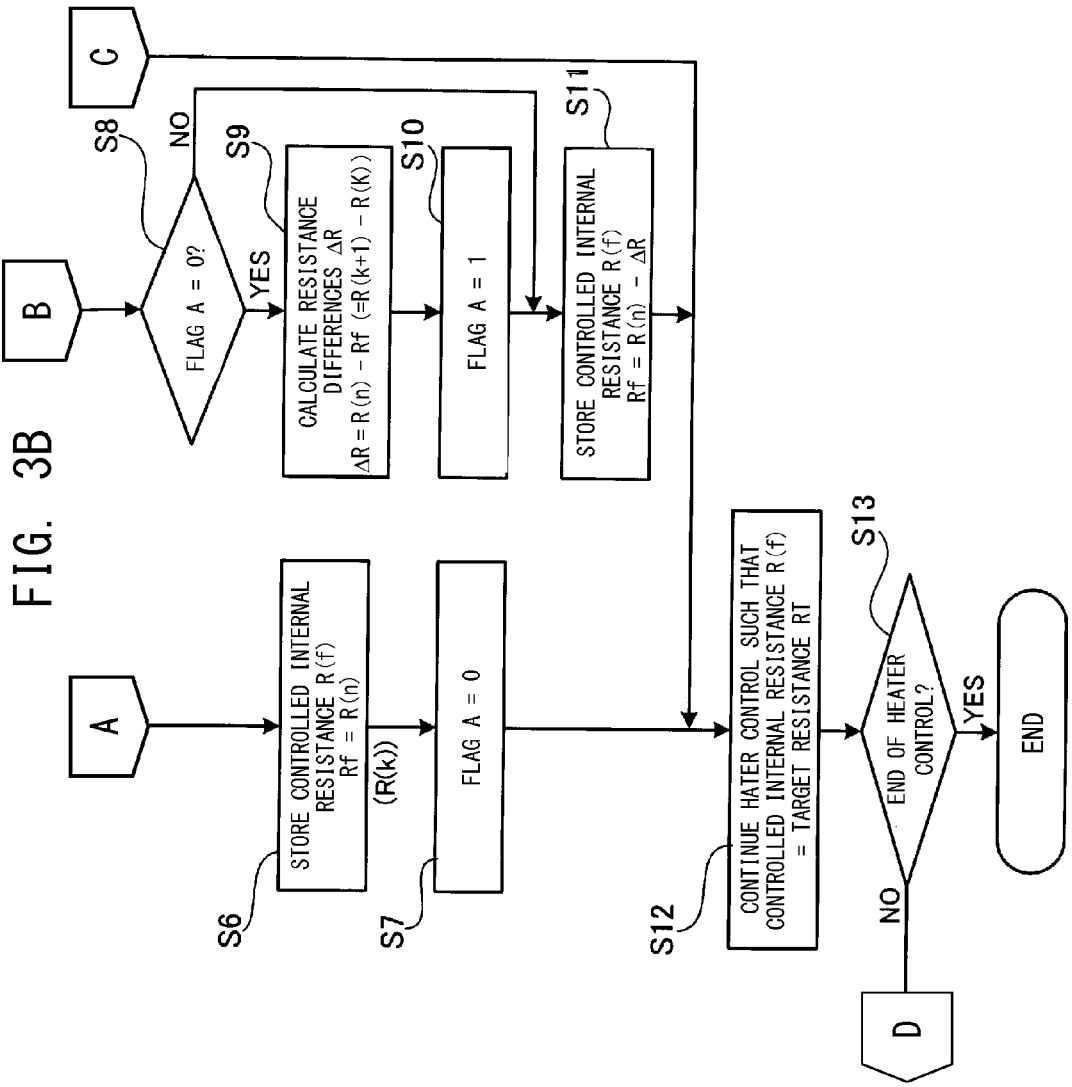

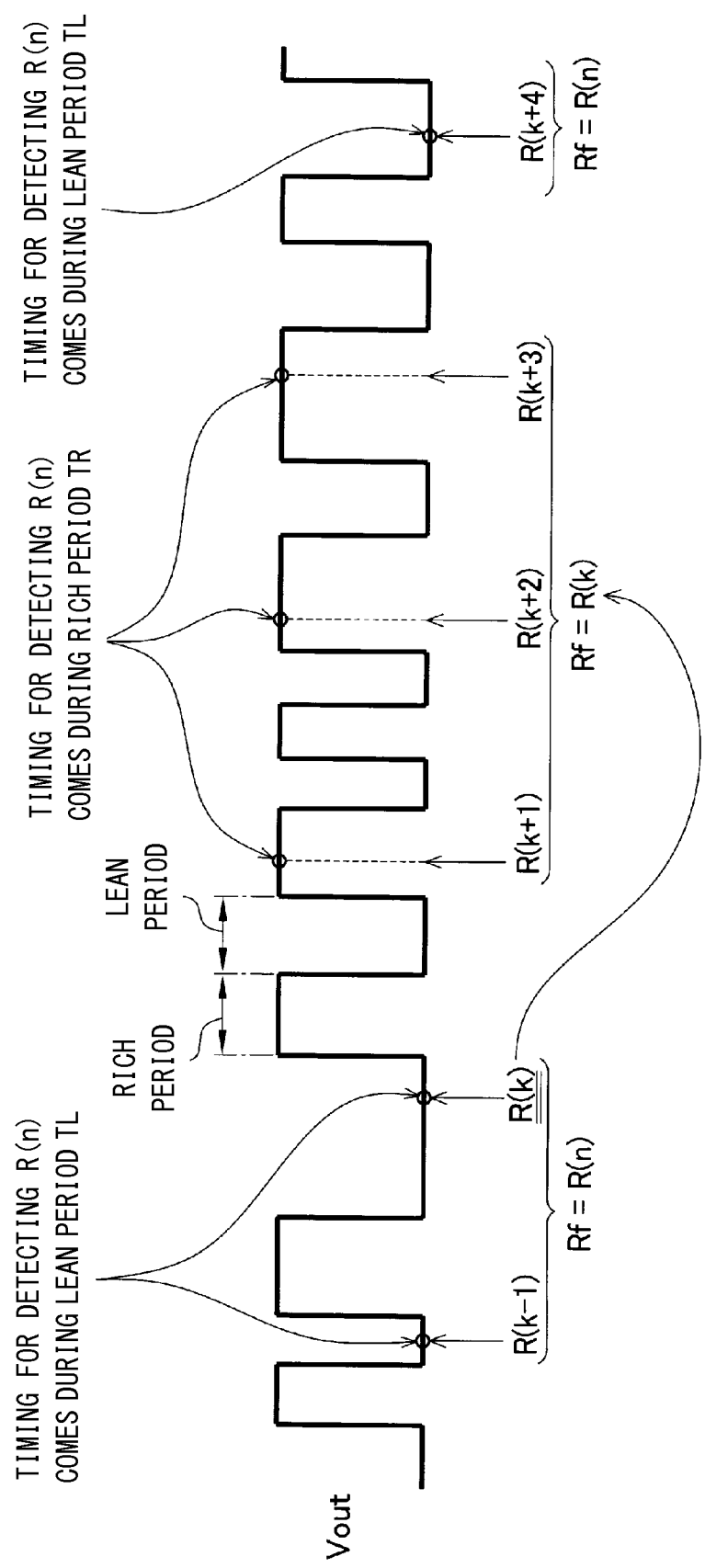

OXYGEN SENSOR CONTROL APPARATUS

TECHNICAL FIELD

The present invention relates to an oxygen sensor control apparatus for controlling an oxygen sensor which is sensible to the concentration of oxygen contained in exhaust gas discharged from an internal combustion engine and which has a characteristic such that its sensor output corresponding to the air-fuel ratio sharply changes around the stoichiometric air-fuel ratio in the course of changing between a lean state and a rich state.

BACKGROUND ART

Conventionally, there has been known an oxygen sensor which is disposed in an exhaust pipe of an internal combustion engine of a vehicle and which responses the concentration of oxygen contained in exhaust gas and detects the air-fuel ratio of the internal combustion engine (i.e., whether the air-fuel ratio is in a rich state or a lean state). The detection element of this oxygen sensor is mainly formed of a solid electrolyte body such as zirconia, and its output voltage (sensor output) corresponding to the air-fuel ratio of the internal combustion engine sharply changes, like a binary value, at the stoichiometric air-fuel ratio. Therefore, by utilizing this phenomenon, it is possible to determine whether the air-fuel ratio of fuel mixture burned in the internal combustion engine is on the rich side or the lean side. Notably, the solid electrolyte body which forms the detection element exhibits sufficiently high oxygen ion conductivity at a high temperature of about 600° C. or higher (active state). Therefore, a heater for heating the detection element is provided in the oxygen sensor so as to heat the detection element to thereby bring the detection element in an active state. Further, by making use of the phenomenon that the element impedance (internal resistance) of the detection element changes in accordance with the element temperature, the supply of electricity to the heater is feedback-controlled such that the element impedance (internal resistance) becomes equal to a target impedance (target resistance) whereby the detection element is maintained at a predetermined temperature within a range in which the detection element is activated. For example, Patent Document 1 discloses an oxygen concentration detection apparatus for an oxygen sensor having a detection element and a heater, which detection apparatus controls the temperature of the detection element by feedback-controlling the power supplied to the heater.

PRIOR ART DOCUMENT

Patent Document

[Patent Document 1] Japanese Patent Application Laid-Open (kokai) No H10-26599

SUMMARY OF THE INVENTION

Problems to be Solved by the Invention

However, such an oxygen sensor which detects (determines) whether the air-fuel ratio is in the rich state or the lean state has a problem in properly controlling the temperature of the detection element. Namely, the detected value of the internal resistance itself is affected by a difference of the air-fuel ratio. Specifically, it has been found that the sensor output of the oxygen sensor affects measurement of the internal resistance, and the value of the internal resistance detected when the air-fuel ratio is in the rich state is greater than that detected when the air-fuel ratio is in the lean state.

Since a variation is produced in the detected internal resistance due to the difference between the rich state and the lean state, it has been difficult to properly control the temperature of the detection element by using the internal resistance. Namely, even when the element temperature does not change, the obtained value of the internal resistance changes depending on whether the air-fuel ratio at the timing for detecting the internal resistance is in the lean state or the rich state. Therefore, even when an attempt is made to control the supply of electricity to the heater such that the obtained value of the internal resistance becomes equal to a target resistance, such control cannot be performed properly.

Notably, the higher the temperature of the detection element, the lower the internal resistance. Therefore, in the case where the supply of electricity to the heater is feedback-controlled such that the internal resistance becomes constant, the internal resistance detected when the air-fuel ratio is in the rich state becomes higher than that detected when the air-fuel ratio is in the lean state, whereby the element temperature is controlled to increase.

Moreover, when the detection element deteriorates because of use or other factors, the internal resistance of the detection element at a certain temperature increases as compared with that before the detection element has deteriorated. In addition, it was found that the variation of the internal resistance due to the difference between the lean state and the rich state increases when the detection element deteriorates.

For example, in the case where a detection element not having deteriorated is heated to 700° C., the internal resistance of the detection element becomes about 30Ω in the lean state and becomes about 35Ω in the rich state. However, after the detection element has deteriorated, even when the detection element is heated to the same temperature (700° C.), the internal resistance of the detection element becomes about 70Ω in the lean state and becomes about 110Ω in the rich state. As descried above, in the case of an oxygen sensor having deteriorated, the internal resistance increases due to deterioration, and at the detection timing in the rich state, the internal resistance is detected to be even higher. Therefore, the control is more likely to become instable.

Such a variation of the internal resistance between the lean state and the rich state is also observed when the temperature of exhaust gas around the oxygen sensor differs. Specifically, the degree of change in the internal resistance corresponding to the difference in the temperature of the exhaust gas becomes larger in the rich state as compared with that in the lean state. Namely, the value of the internal resistance detected in the rich state is more susceptible to the temperature of the surrounding exhaust gas as compared with that detected in the lean state.

The present invention has been accomplished in view of the above-described problems, and provides an oxygen sensor control apparatus which can suppress the influence of the variation of the internal resistance stemming from the difference between the lean state and the rich state, to thereby properly control the temperature of the detection element.

Means for Solving the Problems

One mode of the present invention is an oxygen sensor control apparatus for controlling an oxygen sensor which includes a detection element composed of a solid electrolyte body and a heater for heating the detection element, which is sensible to the concentration of oxygen contained in exhaust gas discharged from an internal combustion engine, and which has a characteristic such that its sensor output corresponding to the air-fuel ratio sharply changes around the stoichiometric air-fuel ratio in the course of changing between a rich state and a lean state, the oxygen sensor control apparatus comprising internal resistance detection means for temporarily changing a voltage between electrodes of the detection element or a current flowing between the electrodes and detecting the internal resistance of the detection element on the basis of the amount of a change in voltage or current which occurs in response to the temporary change; controlled internal resistance obtaining means for obtaining a controlled internal resistance on the basis of the internal resistance; and heater energization control means for feedback-controlling the supply of electricity to the heater such that the controlled internal resistance becomes equal to a target resistance, wherein when a timing for detecting the internal resistance comes during a lean period during which the sensor output indicates that the air-fuel ratio is in the lean state, the controlled internal resistance obtaining means uses the detected internal resistance as the controlled internal resistance, and when a timing for detecting the internal resistance comes during a rich period during which the sensor output indicates that the air-fuel ratio is in the rich state, the controlled internal resistance obtaining means uses, as the controlled internal resistance, a corrected value obtained by correcting the detected internal resistance on the basis of a latest lean resistance which is the last one of the internal resistances detected during lean periods before the detection timing, such that a variation of the internal resistance which stems from the difference between the lean state and the rich state and which is contained in the detected internal resistance is removed.

In this oxygen sensor control apparatus, when a timing for detecting the internal resistance comes during a lean period, the detected internal resistance is used as the controlled internal resistance. Meanwhile, when a timing for detecting the internal resistance comes during a rich period, a corrected value of the internal resistance is used as the controlled internal resistance. In order to properly control the heater, for example, such that the detection element is maintained at a fixed temperature, the detection internals (intervals of detection timings) must be sufficiently short in relation to the responsiveness of the heater to a temperature change. Therefore, when a period corresponding to several to a dozen of detection intervals is observed, the temperature of the detection element is considered to be substantially constant. Accordingly, the internal resistance of the detection element during that period must be constant intrinsically. Namely, the difference between the value of the internal resistance detected at a detection timing during a lean period and that detected at a detection timing during a rich period close to the lean period is considered to be mainly attributable to the difference between the lean state and the rich state. Notably, as having been already described, the value of the internal resistance detected during a rich period is greater than that detected during a lean period, and the detected value of the internal resistance increases when the detection element deteriorates. Also, the detected value of the internal resistance is likely to be influenced by the temperature of exhaust gas around the sensor. In consideration of the influence, the internal resistance detected during a rich period is corrected on the basis of the above-described latest lean resistance detected during the lean period, whereby a variation of the internal resistance which stems from the difference between the lean state and the rich state and which is contained in the detected internal resistance is removed. Thus, not only during lean periods but also during rich periods, it is possible to properly control the supply of electricity to the heater, while suppressing the influence of the variation of the internal resistance, to thereby properly control the temperature of the detection element.

An example of a method of obtaining the "corrected value" from the detected internal resistance is a method of performing correction when the internal resistance is first detected during a rich period after the internal resistance has been detected during a lean period. Specifically, in order to remove the difference (variation) between the internal resistance detected during the lean period and that detected during the rich period; i.e., between the above-described latest lean resistance and a first rich resistance which will be described later, correction is performed in order to render the first rich resistance coincident with the latest lean resistance. A specific example of the correction method is obtaining the difference between the first rich resistance and the latest lean resistance, and, when the internal resistance is subsequently obtained during a rich period, subtracting the difference from the obtained internal resistance, to thereby obtain the "corrected value." Another example of the correction method is obtaining the ratio between the first rich resistance and the latest lean resistance, and dividing the internal resistance subsequently obtained during a rich period by the ratio, to thereby obtain the "corrected value."

In order to detect the internal resistance, the voltage between electrodes of the detection element or the current flowing between the electrodes may be changed temporarily. The internal resistance may be detected on the basis of the amount of a change in voltage or current which occurs in response to the temporary change (hereinafter such an amount of change will be referred to as the "response change amount"). The method and circuit configuration for detecting the internal resistance may be selected freely.

Specifically, for example, one electrode of the detection element is connected to a reference potential, and the other electrode is connected to a power supply voltage line via a reference resistor and a switching element such that a resistor-voltage-division circuit is formed by the detection element and the reference resistor. The current flowing through the electrodes of the detection element is changed temporarily by turning on the switching element. When a current flows through the detection element, a voltage drop corresponding to the internal resistance of the detection element is produced. Therefore, the response change amount of voltage (voltage change amount) which occurs in response to the temporary change reflects the internal resistance. Namely, the internal resistance of the detection element can be detected from this response change amount. Notably, there may be used a method of causing a constant current to temporarily flow between the electrodes of the detection element so as to produce a voltage drop across the internal resistor, to thereby obtain the response change amount of voltage.

In the above-described oxygen sensor control apparatus, preferably, the controlled internal resistance obtaining means obtains, as the corrected value, a value by subtracting a resistance difference from the detected internal resistance, the resistance difference being the difference between the latest lean resistance and a first rich resistance which is the internal resistance first detected during a rich period after the latest lean resistance has been detected, and uses the corrected value as the controlled internal resistance.

In this oxygen sensor control apparatus, the "corrected value" is obtained by subtracting the resistance difference from the detected internal resistance, and is used as the controlled internal resistance. Therefore, the value of the controlled internal resistance becomes equal to a value obtained by adding to the latest lean resistance a change in the internal resistance which is determined on the basis of the first rich resistance and which is contained in the internal resistances detected at respective detection timings having come during rich periods. Accordingly, it is possible to properly control the temperature of the detection element while following the change in the internal resistance.

Another mode of the present invention is an oxygen sensor control apparatus for controlling an oxygen sensor which includes a detection element composed of a solid electrolyte body and a heater for heating the detection element, which is sensible to the concentration of oxygen contained in exhaust gas discharged from an internal combustion engine and which has a characteristic such that its sensor output corresponding to the air-fuel ratio sharply changes around the stoichiometric air-fuel ratio in the course of changing between a rich state and a lean state, the oxygen sensor control apparatus comprising internal resistance detection means for temporarily changing a voltage between electrodes of the detection element or a current flowing between the electrodes and detecting the internal resistance of the detection element on the basis of the amount of a change in voltage or current which occurs in response to the temporary change; controlled internal resistance obtaining means for obtaining a controlled internal resistance on the basis of the internal resistance; and heater energization control means for feedback-controlling the supply of electricity to the heater such that the controlled internal resistance becomes equal to a target resistance, wherein when a timing for detecting the internal resistance comes during a lean period during which the sensor output indicates that the air-fuel ratio is in the lean state, the controlled internal resistance obtaining means uses the detected internal resistance as the controlled internal resistance, and when a timing for detecting the internal resistance comes during a rich period during which the sensor output indicates that the air-fuel ratio is in the rich state, the controlled internal resistance obtaining means uses, as the controlled internal resistance, a latest lean resistance which is the last one of the internal resistances detected during lean periods before the detection timing.

In this oxygen sensor control apparatus, when a timing for detecting the internal resistance comes during a lean period, the detected internal resistance is used as the controlled internal resistance. Meanwhile, when a timing for detecting the internal resistance comes during a rich period, the latest lean internal resistance is used as the controlled internal resistance. In this method, in the case where timings for detecting the internal resistance successively come during rich periods, control which copes with the variation of the internal resistance during the rich periods cannot be performed. However, during these periods, the temperature of the detection element can be maintained substantially constant by using the latest lean resistance without being affected by the variation of the internal resistance stemming from the difference between the lean state and the rich state. Therefore, it is possible to properly control the temperature of the detection element while suppressing the influence of the variation of the internal resistance stemming from the difference between the lean state and the rich state.

BRIEF DESCRIPTION OF THE DRAWINGS

FIGS. 3A and 3B Flowcharts showing operation of a microprocessor of the oxygen sensor control apparatus according to the first embodiment.

FIG. 4 Timing chart showing an example change in air-fuel ratio (lean state and rich state) and timings for detecting the internal resistance and the detail of processing in the case where an oxygen sensor control apparatus according to a second embodiment is applied thereto.

MODE FOR CARRYING OUT THE INVENTION

Embodiment 1

Figure 1:
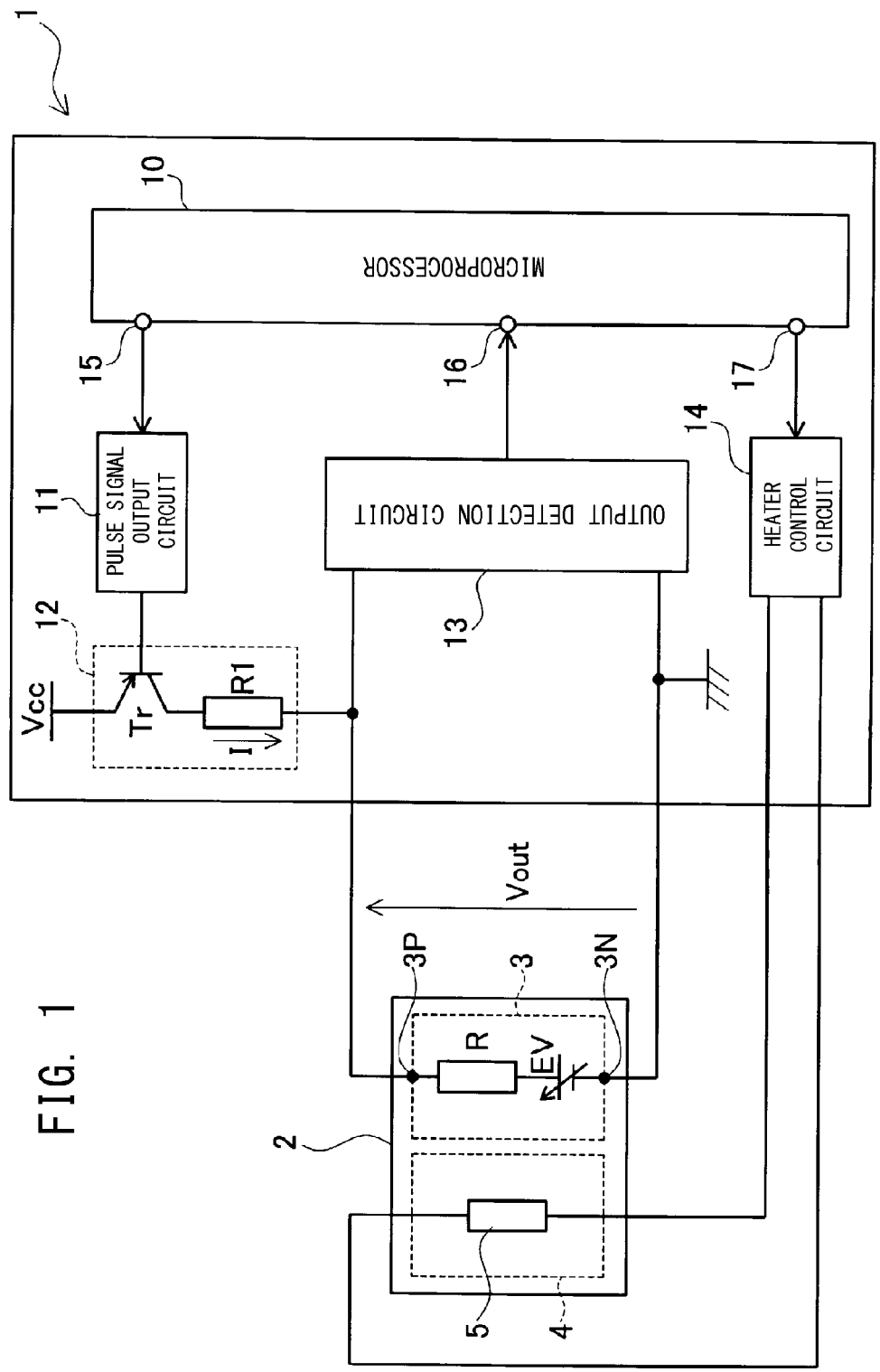
FIG. 1 Explanatory diagram schematically showing the configuration of an oxygen sensor and the configuration of an oxygen sensor control apparatus according to a first embodiment.

A first embodiment of the present invention will now be described with reference to the drawings. FIG. 1 is a diagram schematically showing the configuration of an oxygen sensor control apparatus 1 according to the present first embodiment. The oxygen sensor control apparatus 1 is mounted on a vehicle (not shown) having an unillustrated engine, and is connected to an oxygen sensor 2 so as to control the same. The oxygen sensor control apparatus 1 responses the concentration of oxygen contained in exhaust gas discharged from an internal combustion engine and detects (determines) whether the air-fuel ratio of fuel mixture is shifted to the rich side or the lean side from the stoichiometric air-fuel ratio when the fuel mixture is burned in the internal combustion engine.

This oxygen sensor 2 includes a detection element 3 in which a pair of electrodes 3P and 3N are formed on an oxygen-ion-conductive solid electrolyte body mainly made of zirconia; and a heater 4 for heating the detection element 3. More specifically, one electrode 3N, which is formed on the outer circumferential surface of the detection element 3 composed of the solid electrolyte body having the shape of a cylindrical tube with a bottom, is exposed to the exhaust gas, and the other electrode 3P, which is formed on the inner circumferential surface of the detection element 3, is exposed to a reference gas (atmosphere). The heater 4 having a barlike shape is inserted into the inner space of the detection element 3 having a bottomed-tubular shape, whereby the oxygen sensor 2 is formed. When the detection element 3 composed of the solid electrolyte body is heated by the heater 4 to an activation temperature higher than 600° C. at which the detection element 3 comes into an active state, the detection element 3 exhibits a satisfactory oxygen-ion conductivity. In this state, an electromotive force corresponding to the oxygen concentration is produced between the electrodes 3P and 3N, whereby a sensor output Vout is obtained. The supply of electricity to the heater 4 of the oxygen sensor 2 is controlled by the oxygen sensor control apparatus 1 such that the detection element 3 is maintained at a predetermined temperature within a temperature range in which the detection element 3 comes into the activate state (hereinafter, this range may be referred to as the "activation temperature range").

Notably, the oxygen sensor 2 has a characteristic such that when the detection element 3 is heated to the activation temperature, the sensor output Vout (electromotive force) sharply changes, like a binary value, when the air-fuel ratio approaches the stoichiometric air-fuel ratio in the course of changing between the rich state and the lean state; i.e., the sensor output Vout becomes about 0.05 V in the lean state and becomes about 0.9 V in the rich state.

The heater 4 includes a heat generation resistor 5 mainly made of tungsten or platinum, and is connected to a heater control circuit 14. The heater control circuit 14 is connected to a PWM output port 17 of a microprocessor 10. The electricity is supplied to the heater 4 under PWM control performed by the heater control circuit 14, whereby the detection element 3 is heated. In order to maintain the detection element 3 at a predetermined temperature within the activation temperature range, the duty ratio of pulses used for the PWM control is determined by PID control or PI control performed by the microprocessor 10.

The detection element 3 has an internal resistor having an internal resistance R, which decreases as the temperature of the detection element 3 increases. Namely, a predetermined correlation exists between the internal resistance R and the temperature of the detection element 3. Therefore, the element temperature can be maintained at a predetermined temperature by controlling the internal resistance R such that it becomes equal to a target resistance.

The detection element 3 exhibits oxygen ion conductivity at the activation temperature to thereby function as an oxygen concentration cell, and generates an electromotive force EV corresponding to a difference in oxygen concentration between the electrodes 3N and 3P. Therefore, as shown in FIG. 1, the equivalent circuit of the detection element 3 can be considered to have a series circuit which is located between the electrodes 3P and 3N and which includes a cell (oxygen concentration cell) generating the electromotive force EV and the internal resistor having the internal resistance R.

The electrodes 3P and 3N of the detection element 3 are connected to an output detection circuit 13. The output detection circuit 13 detects the electromotive force EV as the sensor output Vout, and supplies it to an A/D input port 16 of the microprocessor 10. Notably, of the electrodes 3P and 3N of the detection element 3, one electrode 3N is connected to a reference potential (GND) of the output detection circuit 13, and the other electrode 3P is higher in potential than the electrode 3N.

Also, in addition to the output detection circuit 13, a voltage shift circuit 12 is connected to the electrode 3P of the detection element 3. The voltage shift circuit 12 connects the electrode 3P to a power supply voltage line Vcc through a reference resistor having a resistance R1 and a switching element Tr. A pulse signal output circuit 11 is connected to the switching element Tr of the voltage shift circuit 12. The pulse signal output circuit 11 is connected to an I/O port 15 of the microprocessor 10. In accordance with an instruction from the microprocessor 10, the pulse signal output circuit 11 drives the voltage shift circuit 12 so as to temporarily change the current flowing between the electrodes 3P and 3N of the detection element 3. Specifically, the pulse signal output circuit 11 turns on the switching element Tr of the voltage shift circuit 12 such that a current flows from the power supply voltage line Vcc to the reference resistor and then to the detection element 3, to thereby change the sensor output Vout between the electrodes 3P and 3N of the detection element 3 by an amount corresponding to a voltage drop produced across the internal resistor (internal resistance R) of the detection element 3.

When the current flowing through the internal resistor (internal resistance R) and the reference resistor (reference resistance R1) is represented by I and the electromotive force of the oxygen concentration cell formed by the detection element 3 is represented by EV, the magnitude of the current I is given by the following Expression (1).

$$I=(Vcc-EV)/(R1+R) \quad (1)$$

Also, the voltage drop VF produced across the internal resistor (internal resistance R) by the current I is represented by the following Expression (2).

$$VF=R\times(Vcc-EV)/(R1+R) \quad (2)$$

Here, it is assumed that the electromotive force EV before the switching element Tr of the voltage shift circuit 12 is turned on remains the same after the switching element Tr is turned on. In such a case, the output detection circuit 13 can measure the electromotive force EV from the sensor output Vout(OFF) at the time when the switching element Tr is off (the following Expression (3)).

$$Vout(OFF)=EV \quad (3)$$

Meanwhile, since the sensor output Vout(ON) detected by the output detection circuit 13 at the time when the switching element Tr is on is the sum of the voltage drop VF generated across the internal resistor (internal resistance R) and the electromotive force EV, the sensor output Vout(ON) is given by the following Expression (4).

$$Vout(ON)=VF+EV \quad (4)$$

Thus, the difference between the sensor output Vout(ON) and the sensor output Vout(OFF); i.e., a response change amount ΔV of voltage is given by the following Expression (5).

$$\Delta V=Vout(ON)-Vout(OFF)=(VF+EV)-EV=VF \quad (5)$$

Accordingly, the internal resistance R of the detection element 3 can be detected by obtaining this response change amount ΔV and calculating the voltage drop caused by the internal resistor (internal resistance R) by using the following Expression (6) obtained from Expressions (2) and (5).

$$R=R1\times\Delta V/((Vcc-EV)-\Delta V) \quad (6)$$

Notably, since the internal resistance R is obtained as time series data at each of predetermined detection timings, it may be denoted by R(n) (n is an integer representing the order).

However, in the case where the internal resistance R is detected in such a manner, as described above, a different value is obtained as the internal resistance R between the lean state and the rich state. Specifically, a value measured as the internal resistance R in the rich state is larger than that measured in the lean state. Although the reason why the detected value of the internal resistance R changes between the lean state and the rich state is not clear, presumably, such a phenomenon occurs because the degree of conduction of oxygen ions moving within the solid electrolyte body changes between the lean state and the rich state.

Incidentally, in order to properly control the heater, for example, such that the detection element 3 is maintained at a fixed temperature, the detection intervals (intervals of detection timings) must be sufficiently short in relation to the responsiveness of the heater to a temperature change. Therefore, when a period corresponding to several to a dozen of detection intervals is observed, the temperature of the detection element 3 is considered to be substantially constant. Accordingly, the internal resistance R of the detection element 3 during that period must be constant intrinsically. Namely, the difference between the value of the internal resistance R detected at a detection timing during a lean period and that detected at a detection timing during a rich period close to the lean period is considered to be mainly attributable to the difference in the state (the concentration of oxygen contained in a gas under measurement) between the lean state and the rich state. Notably, as having been already described, this variation of the internal resistance R between the lean state and the rich state is also affected by deterioration of the detection element 3. In consideration of the influence of deterioration, it is preferred to use, as a reference, the internal resistance R detected during a lean period during which an increase in the internal resistance R due to deterioration is small.

In view of this, in the oxygen sensor control apparatus 1 of the present first embodiment, in the case where a timing for detecting the internal resistance R comes in the lean state (lean period), the supply of electricity to the heater 4 is controlled by using the detected value of the internal resistance R. Meanwhile, in the case where a timing for detecting the internal resistance R comes in the rich state (rich period), the detected value of the internal resistance R is corrected on the basis of the latest lean resistance (the latest one of the values of the internal resistance R detected during lean periods before that rich period), and the supply of electricity to the heater 4 is controlled by using the corrected value. Thus, it is possible to remove the variation of the detected value of the internal resistance R, which is attributable to the difference between the lean state and the rich state and which is contained in the detected value of the internal resistance R.

Figure 2:
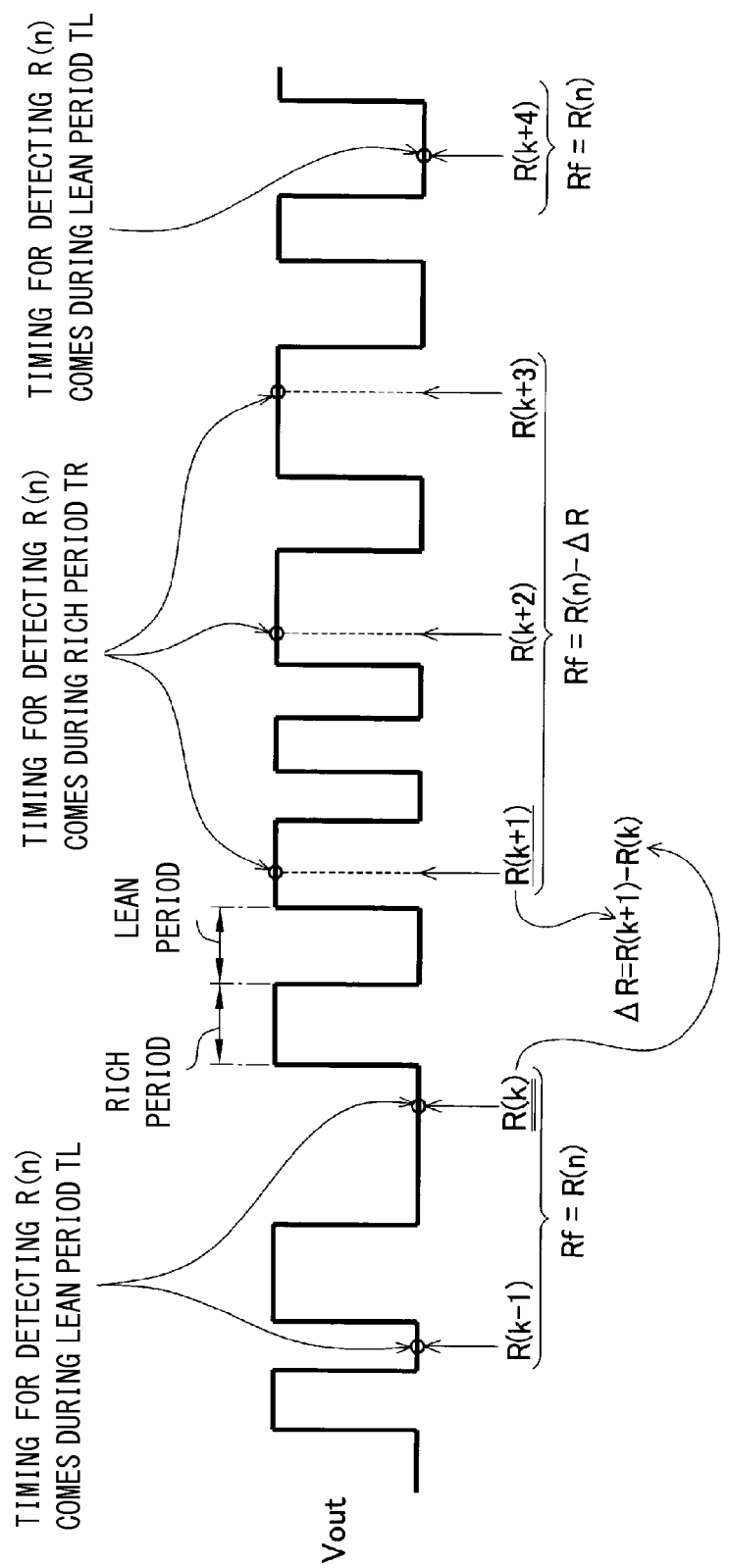
FIG. 2 Timing chart showing an example change in air-fuel ratio (lean state and rich state) and timings for detecting the internal resistance and the detail of processing in the case where the oxygen sensor control apparatus according to the first embodiment is applied thereto.

The control method of the oxygen sensor control apparatus 1 of the present first embodiment will be described more specifically. FIG. 2 is a time chart showing an example change of the air-fuel ratio (the lean state and the rich state), timings for detecting the internal resistance R(n), and the detail of processing in the case where the oxygen sensor control apparatus 1 of the present first embodiment is applied thereto. In FIG. 2, lean periods TL during which the sensor output Vout becomes about 0.05 V and indicates that the air-fuel ratio is in the lean state and rich periods TR during which the sensor output Vout becomes about 0.9 V and indicates that the air-fuel ratio is in the rich state occur alternately and irregularly. In the below, the present first embodiment will be described on the basis of the example of FIG. 2.

Upward arrows in FIG. 2 show timings for detecting the internal resistance R which is performed at predetermined intervals (every 500 msec in the present first embodiment). The measured value of the internal resistance R detected at the n-th timing of these detection timings is denoted by R(n) (hereinafter the measured value will be referred to as the internal resistance R(n)).

It is assumed that as shown in FIG. 2, each of the (k−1)-th and k-th detection timings comes during a lean period TL, and R(k−1) and R(k) are detected as the internal resistance R(n) at the respective timings.

It is also assumed that each of subsequent three ((k+1)-th to (k+3)-th) detection timings comes during a rich period TR, and R(k+1), R(k+2), and R(k+3) are detected as the internal resistance R(n) at the respective timings.

It is further assumed that the subsequent (k+4)-th detection timing comes during a lean period TL, and R(k+4) is detected as the internal resistance R(n).

Of these cases, in the case where the timing for detecting the internal resistance R(n) comes during a lean period TL; i.e., at the (k−1)-th, k-th, and (k+4)-th detection timings, the detected internal resistances R(n) (R(k−1), R(k), R(k+4)) are each stored as a controlled internal resistance Rf (=R(n)) without being corrected. In the oxygen sensor control apparatus 1, the supply of electricity to the heater 4 is controlled by PID control or PI control such that the controlled internal resistance Rf becomes equal to the target resistance RT.

Meanwhile, in the case where the timing for detecting the internal resistance R(n) comes during a rich period TR; i.e., at the (k+1)-th to (k+3)-th detection timings, a value obtained by correcting the detected internal resistances R(n) is used as the controlled internal resistance Rf. Specifically, the internal resistance R(k+1) (first rich resistance) is detected at the (k+1)-th detection timing, which is the first detection timing which comes during a rich period TR after the internal resistance has been detected (in the present example, after R(k) has been obtained) as a result of a detection timing having come during a lean period TL. Also, at the point in time when the (k+1)-th detection timing comes, the value of the internal resistance R(k) (latest lean resistance) which was detected last among the internal resistances R(k−1) and R(k) which were detected during the corresponding lean periods TL at respective timings before the (k+1)-th detection timing is already stored as the controlled internal resistance Rf. At the (k+1)-th detection timing, the difference between the first rich resistance R(k+1) and the latest lean resistance R(k); i.e., the resistance difference $\Delta R(=R(k+1)-R(k))$, is calculated by using these values, and is stored. For R(k+1), R(k+2), and R(k+3) detected at the (k+1)-th to (k+3)-th detection timings which have come during the corresponding rich periods TR, the value $(R(n)-\Delta R)$ obtained by correcting these internal resistances R(k+1), R(k+2), and R(k+3); i.e., by subtracting the resistance difference $\Delta R$ from the internal resistances R(k+1), R(k+2), and R(k+3), are each stored as the controlled internal resistance Rf $(=R(n)-\Delta R)$. The heater control is performed by using this controlled internal resistance Rf.

Notably, the resistance difference $\Delta R(=R(k+1)-R(k))$ used for calculation of the controlled internal resistance Rf is not updated at the (k+2)-th and (k+3)-th detection timings which successively come during the corresponding rich periods TR after the (k+1)-th detection timing. Namely, the resistance difference $\Delta R$ stored at the (k+1)-th detection timing is also used at the (k+2)-th and (k+3)-th detection timings. The value corrected in this manner (controlled internal resistance Rf) becomes equal to a value obtained by adding to the latest lean resistance R(k) a change in the internal resistance which is determined on the basis of the first rich resistance R(k+1) and which is contained in the internal resistances R(n) detected at the detection timings having come during the corresponding rich periods TR (specifically, R(k+1), R(k+2), and R(k+3)).

Next, operation of the microprocessor 10 of the oxygen sensor control apparatus 1 according to the present first embodiment will be described with reference to the flowchart of FIGS. 3A and 3B.

Figure 3A:
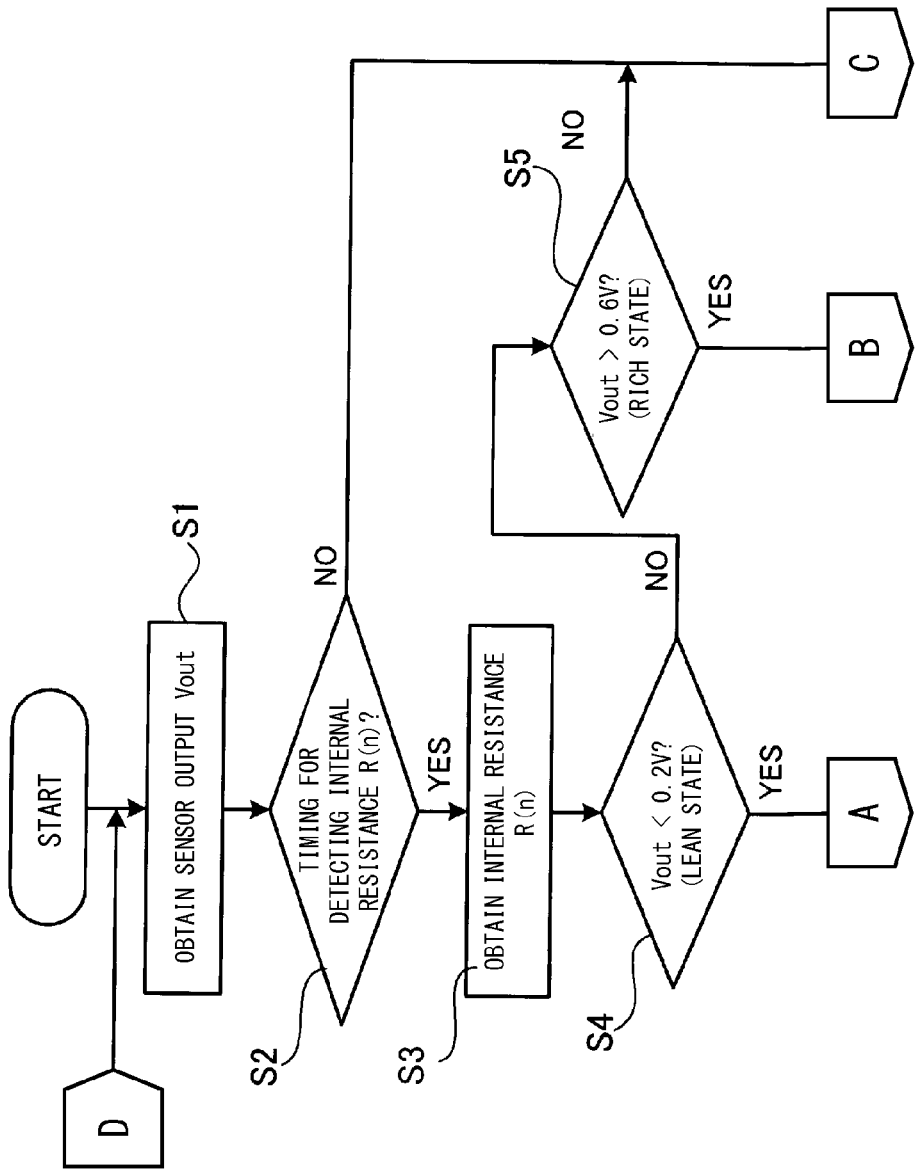

The control program shown in FIGS. 3A and 3B, which is one of the programs executed by the microprocessor 10, shows a flow of processing for obtaining the sensor output Vout, detecting the internal resistance R(n), obtaining the controlled internal resistance Rf, and controlling the supply of electricity to the heater 4.

First, in step S1, the microprocessor 10 obtains the sensor output Vout of the oxygen sensor 2 every time 10 msec elapses. The air-fuel ratio is controlled on the basis of this sensor output Vout. Notably, as described above, in the case where the detection element 3 is maintained at the activation temperature, the sensor output Vout becomes about 0.05 V in the lean state and becomes about 0.9 V in the rich state.

Next, in step S2, the microprocessor 10 determines whether or not a timing for detecting the internal resistance R(n) comes. Since the detection of the internal resistance R(n) is performed at intervals (500 msec) longer than intervals (10 msec) for obtaining the sensor output Vout, in step S2, the microprocessor 10 determines whether or not this detection timing comes. In the case where the detection timing has not yet come (No), the microprocessor 10 proceeds to step S12 so as to control the supply of electricity to the heater 4. Notably, in the case where the microprocessor 10 proceeds to step S12 without detecting the internal resistance R(n) before, the microprocessor 10 controls the supply of electricity to the heater 4 while using, as the controlled internal resistance Rf, a default value stored in the microprocessor 10. Meanwhile, in the case where the detection timing has come (Yes), the microprocessor 10 proceeds to step S3.

In step S3, the microprocessor 10 obtains the internal resistance R(n) of the detection element 3 by using the pulse signal output circuit 11, the voltage shift circuit 12, and the output detection circuit 13.

Next, in step S4, the microprocessor 10 determines on the basis of the magnitude of the sensor output Vout, whether or not the air-fuel ratio at the time when the detection timing has come is in the lean state. In the case where the sensor output Vout is smaller than 0.2 V (Yes), the microprocessor 10 determines that a detection timing has come during a lean period TL during which the air-fuel ratio is in the lean state, and proceeds to step S6. Meanwhile, in other cases (No), the microprocessor 10 proceeds to step S5 and determines on the basis of the magnitude of the sensor output Vout, whether or not the air-fuel ratio at the time when the detection timing has come is in the rich state. In the case where the microprocessor 10 determines in step S5 that the sensor output Vout is larger than 0.6 V (Yes), the microprocessor 10 determines that a detection timing has come during a rich period TR during which the air-fuel ratio is in the rich state, and proceeds to step S8. In other cases (No), the microprocessor 10 proceeds to step S12. In this case, the sensor output Vout is 0.2 V to 0.6 V, which means that the detection timing has come during a stoichiometric period during which the air-fuel ratio is in a stoichiometric region between the lean state and the rich state (in the vicinity of the stoichiometric air-fuel ratio).

In step S6, the microprocessor 10 stores the internal resistance R(n) obtained in step S3 as the controlled internal resistance Rf used for the heater control in step S12, which will be described later (Rf=R(n)). In step S7 subsequent thereto, the microprocessor 10 sets the value of a flag A to 0. The flag A shows whether a resistance difference ΔR to be described later has already been obtained. After that, the microprocessor 10 proceeds to step S12 so as to feedback-control the supply of electricity to the heater 4 such that the controlled internal resistance Rf becomes equal to the target resistance RT.

Meanwhile, in the case where the microprocessor 10 determines that a detection timing has come during a rich period TR (Yes in step S5) and proceeds to step S8, the microprocessor 10 determines whether or not the value of the flag A is 0. In the case where A=0 (Yes); namely, in the case where the resistance difference ΔR has not yet been obtained, the microprocessor 10 proceeds to step S9.

In step S9, the microprocessor 10 calculates the resistance difference ΔR (ΔR=R(n)−Rf). Notably, R(n) used in this calculation is the latest internal resistance R(n) which was detected in step S3 as a result of arrival of a detection timing during a rich period TR, and the value of the flag A is zero at that time. Therefore, as will be described next, a detection timing immediately before that detection timing is not one which has come during a rich period TR. Therefore, this internal resistance R(n) corresponds to the above-described first rich resistance R(k+1). Also, the controlled internal resistance Rf is the last one of the internal resistances R(n) which were obtained at detection timings during lean periods TL before the detection timing during that rich period TR and was stored in step S6. Therefore, the controlled internal resistance Rf corresponds to the above-described latest lean resistance R(k) (see FIG. 2).

In step S10 subsequent thereto, the microprocessor 10 sets the value of the flag A to 1 so as to indicate that the resistance difference ΔR has already been obtained. Notably, in the case where detection timings successively come during rich periods TR after that, since the result of determination in step S8 becomes No, the above-described steps S9 and S10 are not performed. Namely, the above-described steps S9 and S10 are performed only when a detection timing comes during a rich period TR and the previous detection timing did not come during a rich period TR. Accordingly, the resistance difference ΔR calculated in step S9 is held without being updated in the case where detection timings successively come during rich periods TR.

In step S11, the microprocessor 10 calculates the controlled internal resistance Rf by using the resistance difference ΔR (Rf=R(n)−ΔR), and stores it. Notably, the controlled internal resistance Rf obtained in this step is a controlled internal resistance obtained through correction (i.e., the above-described corrected value). After that, the microprocessor 10 proceeds to step S12 so as to control the supply of electricity to the heater 4 such that the controlled internal resistance Rf becomes equal to the target resistance RT.

Notably, in the present first embodiment, when the microprocessor 10 determines in step S5 that a detection timing has come during a stoichiometric period (No), the microprocessor 10 proceeds directly to step S12. Namely, in the case where a detection timing has come during a stoichiometric period, the microprocessor 10 does not update the value of the controlled internal resistance Rf used for heater control, and continues the heater control while using the controlled internal resistance Rf updated at the latest detection timing during a lean period TL or a rich period TR.

In step 13 subsequent to step S12, the microprocessor 10 determines whether or not an end instruction for ending the heater control is issued. In the case where the end instruction is not issued (No), the microprocessor 10 returns to step S1, and re-starts the control program from the step of obtaining the sensor output Vout. Meanwhile, in the case where the end instruction is issued, the microprocessor 10 ends the present control program.

In the present first embodiment, the pulse signal output circuit 11, the voltage shift circuit 12, the output detection circuit 13, and the microprocessor 10 which executes step S3 correspond to the internal resistance detection means. Also, the heater control circuit 14 and the microprocessor 10 which executes step S12 correspond to the heater energization control means. Also, the microprocessor 10 which executes steps S4 through S11 corresponds to the controlled internal resistance obtaining means. As described above, R(n) which is referred to when the resistance difference ΔR is calculated in step S9 corresponds to the first rich resistance R(k+1). Also, Rf which is referred to in step S9 corresponds to the latest lean resistance R(k). The controlled internal resistance Rf which is obtained in step S11 (Rf=R(n)−ΔR) during a rich period TR (Yes in step S5) is the corrected value.

As described above, the oxygen sensor control apparatus 1 of the present first embodiment operates as follows. When a timing for detecting the internal resistance R(n) comes during a lean period TL, the apparatus controls the supply of electricity to the heater 4 by using the detected internal resistance R(n) as the controlled internal resistance Rf. Meanwhile, when a timing for detecting the internal resistance R(n) comes during a rich period TR, the apparatus controls the supply of electricity to the heater 4 by using, as the controlled internal resistance Rf, a value (R(n)−ΔR) obtained by correcting the detected internal resistance (step S11). The corrected value (controlled internal resistance Rf) refers to a value obtained by subtracting the resistance difference ΔR, which is the difference between the first rich resistance R(k+1) and the latest lean resistance R(k), from the newly detected internal resistance R(n). By means of correcting the internal resistance R(n) obtained in a rich period TR by using the resistance difference ΔR as described above, the variation of the internal resistance R(n) which stems from the difference between the lean state and the rich state and which is contained in the obtained internal resistance R(n) can be removed. As a result, the apparatus can properly control the supply of electricity to the heater 4 by suppressing the influence of the variation of the internal resistance R(n) not only during lean periods TL but also during rich periods TR, to thereby properly control the temperature of the detection element 3. Also, the corrected value is a value obtained by adding to the latest lean resistance R(k) a variation of the internal resistance R(n) at each detection timing which comes during a rich period TR in relation to the first rich resistance R(k+1). Therefore, the apparatus can properly control the temperature of the detection element 3 while following the variation of the internal resistance R(n) which occurs over rich periods TR.

Furthermore, the variation of the internal resistance R(n) attributable to the difference between the lean state and the rich state appears more remarkably during rich periods TR when the detection element 3 has deteriorated. However, this influence of deterioration can also be suppressed.

Second Embodiment

Next, a second embodiment will be described. In the first embodiment, when a timing for detecting the internal resistance R(n) comes during a lean period TL, the supply of electricity to the heater 4 is controlled with the detected internal resistance R(n) being used as the controlled internal resistance Rf without correction. Meanwhile, when a timing for detecting the internal resistance R(n) comes during a rich period TR, the supply of electricity to the heater 4 is controlled with the value ((R(n)−ΔR) obtained by correcting the detected internal resistance R(n) being used as the controlled internal resistance Rf. The present second embodiment is identical with the first embodiment shown in FIG. 1 except the point that when a timing for detecting the internal resistance R(n) comes during a rich period TR, the supply of electricity to the heater 4 is controlled with the latest lean resistance R(k) being used as the controlled internal resistance Rf (=R(k)). Therefore, the point differing from the first embodiment will be mainly described, and descriptions of portions similar to those of the first embodiment are omitted or simplified.

FIG. 4 is a timing chart showing an example change in air-fuel ratio (lean state and rich state) and timings for detecting the internal resistance R(n) and the detail of processing in the case where an oxygen sensor control apparatus 1 according to the present second embodiment is applied thereto. In FIG. 4, like the example in the first embodiment, lean periods TL during which the sensor output Vout becomes about 0.05 V and indicates that the air-fuel ratio is in the lean state and rich periods TR during which the sensor output Vout becomes about 0.9 V and indicates that the air-fuel ratio is in the rich state occur alternately and irregularly. In the below, the present second embodiment will be described on the basis of the example of FIG. 4.

Upward arrows in FIG. 4 show timings for detecting the internal resistance R which is performed at predetermined intervals (every 500 msec in the present second embodiment). The measured value of the internal resistance R detected at the n-th timing of these detection timings is denoted by R(n) (hereinafter the measured value will be referred to as the internal resistance R(n)).

In FIG. 4 as well, as in the case of the example shown in FIG. 2, it is assumed that each of the successive (k−1)-th and k-th detection timings comes during a lean period TL, and R(k−1) and R(k) are detected as the internal resistance R(n) at the respective timings. It is also assumed that each of subsequent three ((k+1)-th to (k+3)-th) detection timings comes during a rich period TR, and R(k+1), R(k+2), and R(k+3) are detected as the internal resistance R(n) at the respective timings. It is further assumed that the subsequent (k+4)-th detection timing comes during a lean period TL, and R(k+4) is detected as the internal resistance R(n).

Of these cases, in the case where the timing for detecting the internal resistance R(n) comes during a lean period TL; i.e., at the (k−1)-th, k-th, and (k+4)-th detection timings, the detected internal resistances R(n) (R(k−1), R(k), R(k+4)) are each stored as a controlled internal resistance Rf (=R(n)) without being corrected. In the oxygen sensor control apparatus 1, the supply of electricity to the heater 4 is controlled by PID control or PI control such that the controlled internal resistance Rf becomes equal to the target resistance RT.

Meanwhile, in the case where the timing for detecting the internal resistance R(n) comes during a rich period TR; i.e., at the (k+1)-th to (k+3)-th detection timings, none of the detected internal resistances R(n) (specifically, R(k+1), R(k+2), and R(k+3)) is used for heater control. In the present second embodiment, the value of the internal resistance R(k) (latest lean resistance) which was detected last among the internal resistances R(k−1) and R(k) which were detected during the corresponding lean periods TL at respective timings before the (k+1)-th to (k+3)-th detection timings which come during these rich periods TR is used as the controlled internal resistance Rf (=R(k)). Specifically, in the case where a detection timing comes during a rich period, the controlled internal resistance Rf stored at the detection timing having come during a lean period TL is not updated. Thus, the latest lean resistance R(k), which is detected last during the lean periods TL, remains stored as the controlled internal resistance Rf. The heater control is performed by using this controlled internal resistance Rf.

Notably, in the present second embodiment, the internal resistance R(n) is detected at each of detection timings which come during rich periods TR. However, as described above, the detected internal resistance R(n) is not used for the heater control. Therefore, the second embodiment may be modified such that the internal resistance R(n) is not detected when detection timings come during rich periods TR.

Next, operation of the microprocessor 10 of the oxygen sensor control apparatus 1 according to the present second embodiment will be described with reference to the flowchart of FIG. 5.

Figure 5:
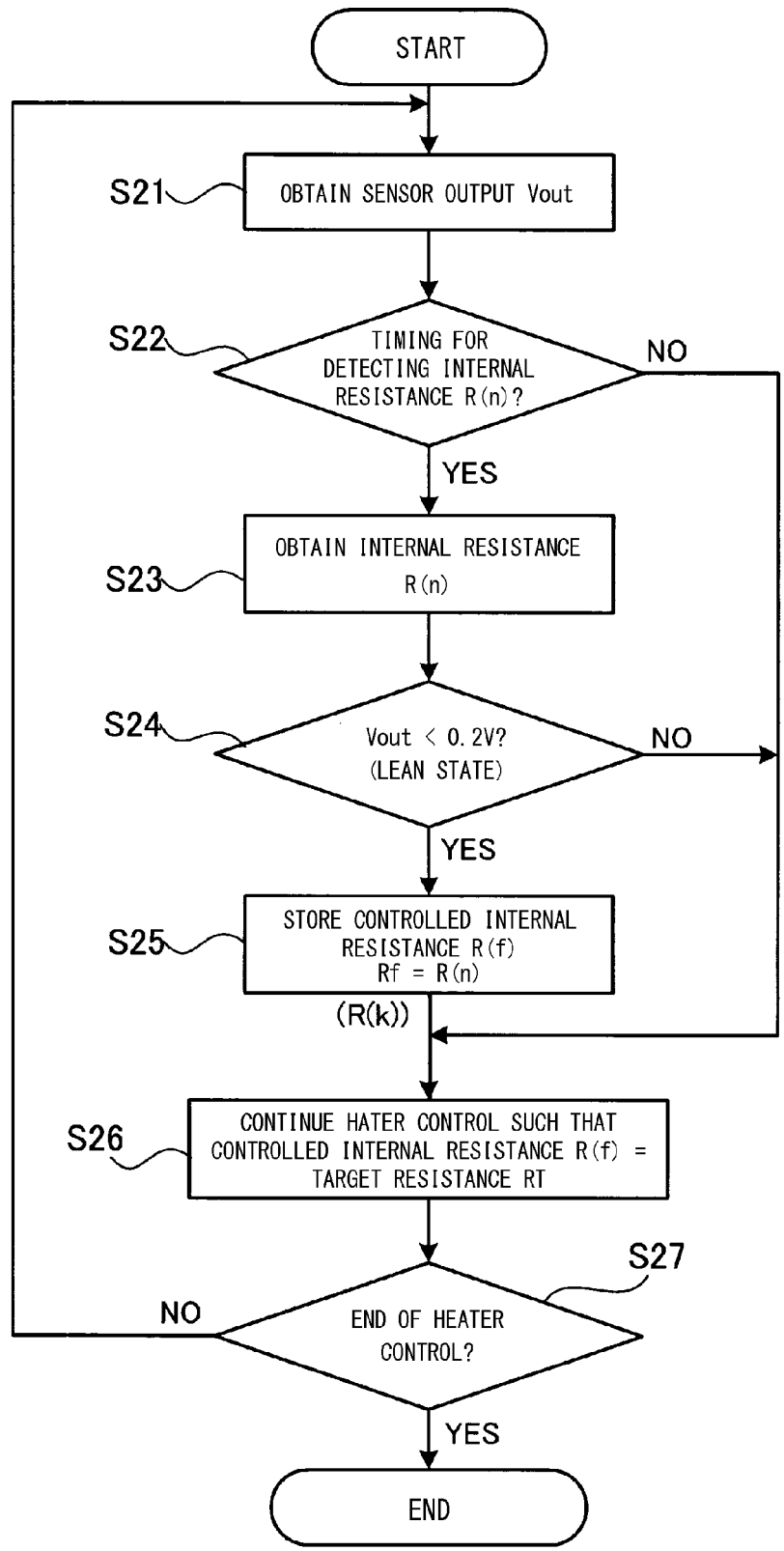
FIG. 5 Flowchart showing operation of a microprocessor of the oxygen sensor control apparatus according to the second embodiment.

The control program shown in FIG. 5, which is one of the programs executed by the microprocessor 10, shows a flow of processing for obtaining the sensor output Vout, detecting the internal resistance R(n), obtaining the controlled internal resistance Rf, and controlling the supply of electricity to the heater 4 as in the case of the first embodiment.

First, in step S21, the microprocessor 10 obtains the sensor output Vout of the oxygen sensor 2 every time 10 msec elapses. The air-fuel ratio is controlled on the basis of this sensor output Vout. Notably, as described above, in the case where the detection element 3 is maintained at the activation temperature, the sensor output Vout becomes about 0.05 V in the lean state and becomes about 0.9 V in the rich state.

Next, in step S22, the microprocessor 10 determines whether or not a timing for detecting the internal resistance R comes. Since the detection of the internal resistance R is performed at intervals (500 msec) longer than intervals (10 msec) for obtaining the sensor output Vout, in step S22, the microprocessor 10 determines in step S22 whether or not this detection timing has come. In the case where the detection timing has not yet come (No), the microprocessor 10 proceeds to step S26 so as to control the supply of electricity to the heater 4. Meanwhile, in the case where the detection timing has come (Yes), the microprocessor 10 proceeds to step S23.

In step S23, the microprocessor 10 obtains the internal resistance R(n) of the detection element 3 by using the pulse signal output circuit 11, the voltage shift circuit 12, and the output detection circuit 13.

Next, in step S24, the microprocessor 10 determines on the basis of the magnitude of the sensor output Vout, whether or not the air-fuel ratio at the time when the detection timing has come is in the lean state. In the case where the sensor output Vout is smaller than 0.2 V (Yes), the microprocessor 10 determines that a detection timing has come during a lean period TL during which the air-fuel ratio is in the lean state, and proceeds to step S25. Meanwhile, in other cases (where a detection timing has come during a rich period TR or during a stoichiometric period) (No), the microprocessor 10 proceeds to step S26.

In step S25, the microprocessor 10 stores, as the controlled internal resistance Rf, the internal resistance R(n) obtained in step S23 (Rf=R(n)). Subsequently, the microprocessor 10 proceeds to step S26 so as to continue the energization control for the heater 4 such that the controlled internal resistance Rf becomes equal to the target resistance RT.

Meanwhile, in the case where the microprocessor 10 makes a "No" determination in step S24 (namely, in the case where a detection timing has come during a rich period TR or during a stoichiometric period), the microprocessor 10 proceeds directly to step S26, which is the step for heater control. Therefore, in the case where a detection timing has come during a rich period TR or during a stoichiometric period, the value of the controlled internal resistance Rf used for the heater control is not updated. Accordingly, in these cases, the microprocessor 10 performs the heater control in the step S26 while using the controlled internal resistance Rf (=R(k)) which is the last one of the internal resistances R(k−1) and R(k) obtained during the lean periods TL before the rich period TR or the stoichiometric period. Namely, the microprocessor 10 uses the latest lean resistance R(k) as the controlled internal resistance Rf (see FIG. 4).

In step S27 subsequent to step S26, the microprocessor 10 determines whether or not an end instruction for ending the heater control is issued. In the case where the end instruction is not issued (No), the microprocessor 10 returns to step S21, and re-starts the control program from the step of obtaining the sensor output Vout. Meanwhile, in the case where the end instruction is issued, the microprocessor 10 ends the present control program.

In the present second embodiment, the pulse signal output circuit 11, the voltage shift circuit 12, the output detection circuit 13, and the microprocessor 10 which executes step S23 correspond to the internal resistance detection means. Also, the heater control circuit 14 and the microprocessor 10 which executes step S26 correspond to the heater energization control means. Also, the microprocessor 10 which executes steps S24 and S25 corresponds to the controlled internal resistance obtaining means.

As described above, the oxygen sensor control apparatus 1 of the present second embodiment operates as follows. When a timing for detecting the internal resistance R(n) comes during a lean period TL, the apparatus controls the supply of electricity to the heater 4 by using the detected internal resistance R(n) as the controlled internal resistance Rf. Meanwhile, when a timing for detecting the internal resistance R(n) comes during a rich period TR, the apparatus controls the supply of electricity to the heater 4 by using the latest lean resistance R(k) as the controlled internal resistance Rf. Therefore, in the case where timings for detecting the internal resistance R(n) successively come during rich periods TR, the apparatus cannot perform the heater control while coping with the variation of the internal resistance R(n) which occurs during the rich periods TR. However, during these periods, the temperature of the detection element 3 can be maintained substantially constant by using the latest lean resistance R(k) without being affected by the variation of the internal resistance R(n) stemming from the difference between the lean state and the rich state. Therefore, it is possible to properly control the temperature of the detection element 3 while suppressing the influence of the variation of the internal resistance R(n) stemming from the difference between the lean state and the rich state.

Although the first and second embodiments of present invention have been described, needless to say, the present invention is not limited to the first and second embodiments, and may be freely modified for application without departing from the scope of the present invention.

For example, in the first embodiment, the corrected value (R(n)−ΔR) is obtained by subtracting the resistance difference ΔR, which is the difference between the first rich resistance R(k+1) and the latest lean resistance R(k), from the internal resistance R(n) detected in each rich period TR. However, the corrected value (e.g., R(k+2)/[R(k+1)/R(k)]) may be obtained by dividing the internal resistance R(n) detected in each rich period TR (e.g., R(k+2)) by the ratio R(k+1)/R(k) between the first rich resistance R(k+1) and the latest lean resistance R(k).

Also, the first and second embodiments are configured such that when the internal resistance R(n) is detected, the current flowing between the electrodes 3P and 3N of the detection element 3 is temporarily changed by using the pulse signal output circuit 11 and the voltage shift circuit 12 (see FIG. 1), and the response change amount ΔV of voltage which responds to this change is obtained. However, the method and circuit configuration for detecting the internal resistance R(n) may be properly changed so as to temporarily change the voltage between the electrodes 3P and 3N of the detection element 3 and obtain the response change amount of the current which responds to this change.

DESCRIPTION OF SYMBOLS

1: oxygen sensor control apparatus
2: oxygen sensor
3: detection element
3P, 3N: electrode
4: heater
R: internal resistance
Vout: sensor output
10: microprocessor
11: pulse signal output circuit (internal resistance detection means)
12: voltage shift circuit (internal resistance detection means)
13: output detection circuit (internal resistance detection means)

14: heater control circuit (heater energization control means)
TL: lean period
TR: rich period
R(n): internal resistance (measured value)
Rf: controlled internal resistance
RT: target resistance
R(k): latest lean resistance
R(k+1): first rich resistance
ΔR: resistance difference
S3, S23: internal resistance detection means
S12, S26: heater energization control means
S4 to S11, S24 to S25: controlled internal resistance obtaining means

The invention claimed is:

1. An oxygen sensor control apparatus for controlling an oxygen sensor which includes a detection element composed of a solid electrolyte body and a heater for heating the detection element, which is sensitive to the concentration of oxygen contained in exhaust gas discharged from an internal combustion engine, and which has a characteristic such that its sensor output corresponding to the air-fuel ratio sharply changes around the stoichiometric air-fuel ratio in the course of changing between a rich state and a lean state, the oxygen sensor control apparatus comprising:
internal resistance detection means for temporarily changing a voltage between electrodes of the detection element or a current flowing between the electrodes and detecting the internal resistance of the detection element on the basis of the amount of a change in voltage or current which occurs in response to the temporary change;
controlled internal resistance obtaining means for obtaining the detected internal resistance as a controlled internal resistance when a timing for detecting the internal resistance comes during a lean period during which the sensor output indicates that the air-fuel ratio is in the rich state and obtaining, as the controlled internal resistance, a corrected value obtained by correcting the detected internal resistance on the basis of a latest lean resistance which is the last one of the internal resistances detected during lean periods before the detection timing, such that a variation of the internal resistance which stems from a difference between the lean state and the rich state and which is contained in the detected internal resistance is removed when a timing for detecting the internal resistance comes during a rich period during which the sensor output indicates that the air-fuel ratio is in the rich state; and
heater energization control means for feedback-controlling the supply of electricity to the heater such that the controlled internal resistance becomes equal to a target resistance.

2. An oxygen sensor control apparatus according to claim 1, wherein the controlled internal resistance obtaining means comprises means for obtaining, as the corrected value, a value by subtracting a resistance difference from the detected internal resistance, the resistance difference being the difference between the latest lean resistance and a first rich resistance which is the internal resistance first detected during a rich period after the latest lean resistance has been detected, and uses the corrected value as the controlled internal resistance.

3. An oxygen sensor control apparatus for controlling an oxygen sensor which includes a detection element composed of a solid electrolyte body and a heater for heating the detection element, which is sensitive to the concentration of oxygen contained in exhaust gas discharged from an internal combustion engine and which has a characteristic such that its sensor output corresponding to the air-fuel ratio sharply changes around the stoichiometric air-fuel ratio in the course of changing between a rich state and a lean state, the oxygen sensor control apparatus comprising:
internal resistance detection means for temporarily changing a voltage between electrodes of the detection element or a current flowing between the electrodes and detecting the internal resistance of the detection element on the basis of the amount of a change in voltage or current which occurs in response to the temporary change;
controlled internal resistance obtaining means for obtaining the detected internal resistance as a controlled internal resistance when a timing for detecting the internal resistance comes during a lean period during which the sensor output indicates that the air-fuel ratio is in the lean state and obtaining, as the controlled internal resistance, a latest lean resistance which is the last one of the internal resistances detected during lean periods before the detection timing when a timing for detecting the internal resistance comes during a rich period during which the sensor output indicates that the air-fuel ratio is in the rich state; and
heater energization control means for feedback-controlling the supply of electricity to the heater such that the controlled internal resistance becomes equal to a target resistance.

* * * * *